US00PP15415P2

(12) United States Plant Patent
Thomsen

(10) Patent No.: US PP15,415 P2
(45) Date of Patent: Dec. 7, 2004

(54) ***EUPHORBIA MILII* PLANT NAMED 'KRONOS'**

(50) Latin Name: *Euphorbia milii*
Varietal Denomination: Kronos

(75) Inventor: Steen Thomsen, Hjortebjerg (DK)

(73) Assignee: Gartneriet Hjortebjerg I/S (DK)

( * ) Notice: Subject to any disclaimer, the term of this patent is extended or adjusted under 35 U.S.C. 154(b) by 0 days.

(21) Appl. No.: 10/799,690

(22) Filed: Mar. 15, 2004

(51) Int. Cl.[7] ..... A01H 5/00
(52) U.S. Cl. ..... Plt./302
(58) Field of Search ..... Plt./302

(56) References Cited

U.S. PATENT DOCUMENTS

PP4,931 P * 11/1982 Stirnadel ..... Plt./302
PP6,212 P * 6/1988 Georgusis ..... Plt./302
PP6,462 P * 12/1988 Stirnadel ..... Plt./302

* cited by examiner

*Primary Examiner*—Bruce R. Campell
*Assistant Examiner*—W C Haas
(74) *Attorney, Agent, or Firm*—Foley & Lardner, LLP

(57) ABSTRACT

A new distinct cultivar of *Euphorbia milii* plant named 'Kronos', characterized by its light red to red-purple floral bract color from 50C to 58B; very low and bushy plant form; vigorous growth habit; larger, green flowers on thick gray-brown peduncles, RHS 199B.

2 Drawing Sheets

Latin name of the genus and species of the plant claimed: *Euphorbia milii* Desmoul.
Variety denomination: 'Kronos'.

BACKGROUND OF THE INVENTION

The present Invention relates to a new and distinct cultivar of *Euphorbia milii* plant, botanically known as *Euphorbia milii* Desmoul, commonly known by the name Crown of Thorns, and hereinafter referred to by the name 'Kronos'.

The new *Euphorbia milii* is a product of a planned breeding program conducted by the Inventor, Steen Thomsen, in Haarslev, Fyn, Denmark. The new *Euphorbia milii* originated from a cross made in 2001 by the Inventor with unnamed cultivars of *Euphorbia milii* Desmoul. The male and female parental cultivars are unnamed, unpatented seedlings of *Euphorbia milii* Desmoul. The Inventor selected the new *Euphorbia milii* cultivar as a single plant from the progeny of the above crossing in 2001 on the basis of its flower color and compact, freely branching habit. Plants of the new *Euphorbia milii* are small, compact and have a unique color, large leaves and abundant medium sized flowers.

A sexual reproduction of the new cultivar by terminal cuttings taken and propagated and trial production batches at Hjortebjerg Nurseries, Denmark, has shown that the unique features of this new *Euphorbia milii* are stable and reproduced true to type in many successive generations.

BRIEF SUMMARY OF THE INVENTION

The following traits have been repeatedly observed and are determined to be the unique characteristics of 'Kronos'. These characteristics in combination distinguish 'Kronos' as a new and distinct cultivar:

1. Light red to red-purple floral bract color from 50C to 58B.
2. Very low and bushy plant form.
3. Vigorous growth habit.

4. Larger, green flowers on thick gray-brown peduncles, RHS 199B.

Plants of the cultivar 'Kronos' can be compared to plants of the cultivar *Euphorbia milii* 'Themis' (unpatented). In side-by-side comparisons conducted by the Inventor in Haarslev, Denmark, plants of the cultivar 'Kronos' and the cultivar 'Themis' differ in the following characteristics:

1. Plants of the new *Euphorbia milii* have light red to red-purple colored bracts and staminate cyathia with orange glands.
2. Plants of the new *Euphorbia milii* have larger dark green leaves than 'Themis'.
3. Plants of the new *Euphorbia milii* have shorter and stiffer peduncles than plants of the cultivar 'Themis'.
4. Plants of the new *Euphorbia milii* are more compact and less branched than the plants of the cultivar 'Themis'.

Plants of the cultivar 'Kronos' have not been observed under all possible environmental conditions. The phenotype may vary somewhat with variations in environment such as temperature, light intensity, day length, and fertility level without, however, any variance in genotype.

BRIEF DESCRIPTION OF THE PHOTOGRAPHS

The accompanying color photographs illustrate the overall appearance and details of flower form, color and structures of the new cultivar, showing the colors as true as it is reasonably possible to obtain in color reproductions of this type. Colors in the photographs may differ slightly from the color values cited in the detailed botanical description, which more accurately describe the actual colors of the new *Euphorbia milii.*

The first photograph shows a full view of a typical full flowering plant of 'Kronos', as grown in an 11 cm pot.

The second photograph shows a close up of the young and older floral cymes of 'Kronos'.

DETAILED BOTANICAL DESCRIPTION

In the following description, color references are made to The Royal Horticultural Society Colour Chart, 4th edition, where general terms of ordinary dictionary significance are used. Plants were grown under greenhouse conditions. Plants used for this description were grown for about 17 weeks after cutting and produced in 6 cm pots. Other pot sizes can be used and the plants are intended for indoor use or as a bedding plant in temperate climates while it is a perennial garden plant in tropical and subtropical areas.

Botanical classification: *Euphorbia milii* Desmoul. 'Kronos'. Euphorbiaceae, Spurge family.

Parentage:

*Female parent.*—Unnamed seedling plant of *Euphorbia milii.*

*Male parent.*—Unnamed seedling plant of *Euphorbia milii.*

Propagation:

*Type cutting.*—Terminal vegetative cuttings taken from plants kept in the vegetative stage by shading and high temperatures (25 C).

*Time to initiate roots.*—About 10 to 14 days at 18 to 21 C in tunnels in a greenhouse.

*Root description.*—Fine, well branched.

Plant description:

*Form.*—Perennial plant with upright plant habit. *Euphorbia milii* 'Kronos' flowers in cymes with cyathia subtended by colored bracts. Freely branching with about 3 lateral flowering branches forming at every node; dense and bushy. Stems are square to pentagonal with ridges—about 10 mm thick at the base. By each node appears groups of thorns: 1 large 12 mm and 4–5 smaller 5 mm. Young thorns are green: 148A; while the older ones becomes stiffer and changes color to gray (199B).

*Crop time.*—After rooting, about 17 weeks are required to produce finished flowering plants in 6 cm pots.

*Plant height* (*soil level to top of plant plane*).—About 12 cm. Width: 21 cm.

*Vigor.*—Vigorous growth rate.

Foliage description: Leaves alternate, single, obovate, entire. Length: 12 cm. Width: About 40 mm. Apex: acute with a small (1 mm) thorn-like appendage. Base: cuneate to almost decussate. Texture: smooth, waxy, dull., glabrous. Color: Young foliage, upper and lower surfaces: 146A and 146C, yellow-green. Mature foliage, upper and lower surfaces: 139A and 148B respectively. Venation, 148D.

Flower description:

*Flower arrangement and shape.*—Floral arrangements composed of cymes. The flowers (cyathia) are starkly reduced so only a circle of 5 glands and the reproductive organs are present. Subtending the cyathia are two colored bracts. The flowers are further complicated by the unique feature of funnel shaped floral buds appearing at the base of the bracts in two or more layers.

*Natural flowering season.*—Continuous throughout the spring and summer in subtropical and tropical regions. In colder climates season can be extended by greenhouse production with high temperatures and supplementary irradiance.

*Flower longevity on the plant.*—5 to 9 weeks; longevity of individual flowers is highly dependent on temperature and light conditions. Bracts turn green with age. Entire cymes drop after withering.

*Inflorescence size.*—Diameter: About 3–5 cm, height: 10 cm.

*Flowers.*—3 mm diameter, Bracts: overlapping at base, ovoid to inverted cordate, approximately 10 mm in length by 17 mm in width; color from 50C to 58B during development.

*Glands.*—5, from 25A shiny orange to 28A during development.

*Anthers.*—Appear after flowers mature; stamen and pollen color 59A, yellow-orange.

*Pistil and stigma.*—Appear before cyathia mature; color 58B to 58C, greenish-yellow.

*Peduncle.*—Strength: strong. Length: About 6 cm. Diameter: About 3 mm. Color: 199B, gray-brown at an angle of 45°.

*Pedicels.*—10 cm long, 2 mm thick; strong; color: 153A, yellow-green.

Weather tolerance: Plants of the new *Euphorbia milii* have exhibited good tolerance to draught, rain and wind, however flowering may cease during cold and dark periods (<15C).

Pest tolerance: Plants of the new *Euphorbia milii* have exhibited good tolerance to following fungi: Mildew, and Thivaliopis. Also, they appear to be less infected by Thrips (Franklinellea).

I claim:

1. A new and distinct cultivar of *Euphorbia milii* plant named 'Kronos', as illustrated and described herein.

* * * * *

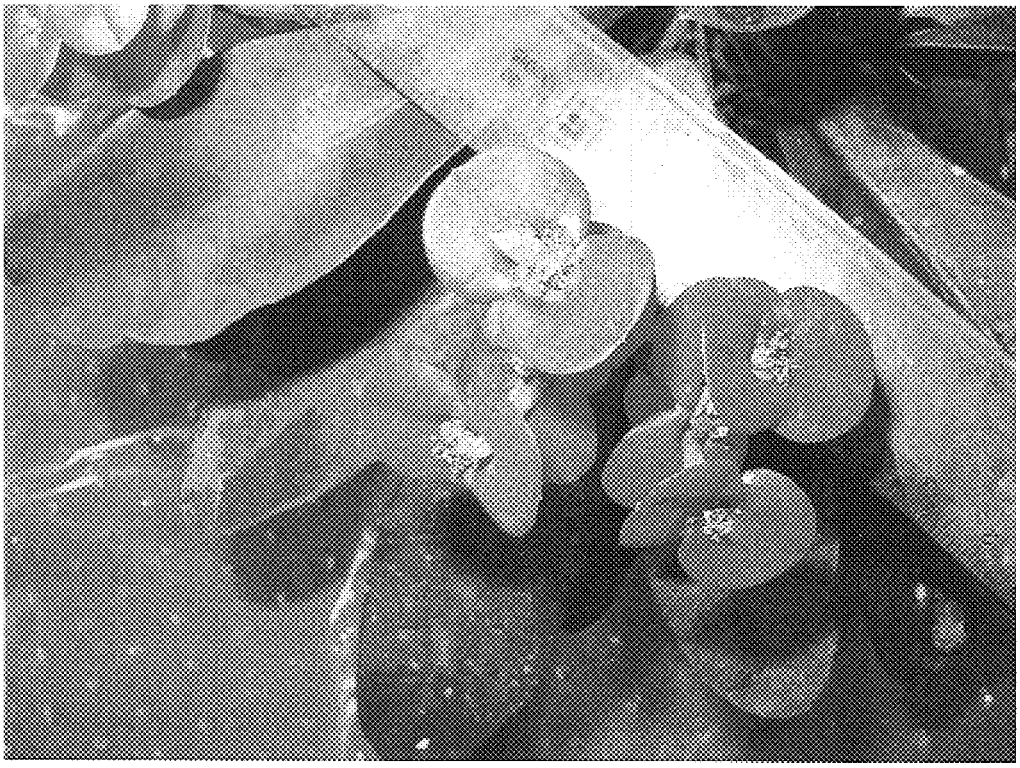

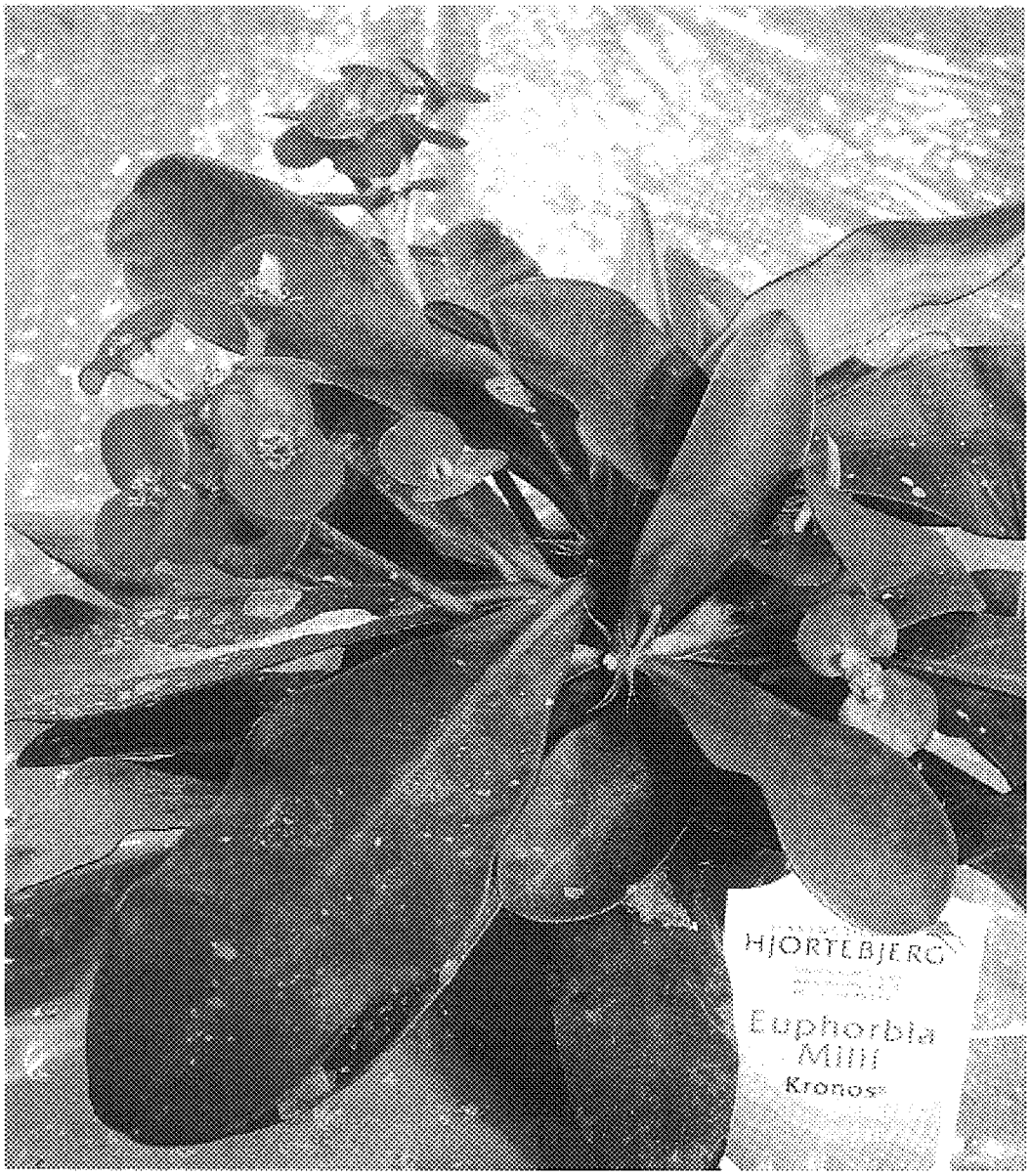
HJORTEBJERG
Euphorbia
Milii
Kronos